United States Patent [19]

Choi et al.

[11] Patent Number: 5,627,300
[45] Date of Patent: May 6, 1997

[54] CARBAMATE COMPOUNDS CONTAINING THIOCARBAMOYL GROUP AND PROCESS FOR PREPARING THE SAME

[75] Inventors: Yong M. Choi, Towaco, N.J.; Dong I. Han; Hyung C. Kim, both of Taejon, Rep. of Korea

[73] Assignee: Yukong Limited, Seoul, Rep. of Korea

[21] Appl. No.: 582,498

[22] Filed: Jan. 3, 1996

[30] Foreign Application Priority Data

Jan. 3, 1995 [KR] Rep. of Korea ............... 1995-17

[51] Int. Cl.$^6$ ............................................. C07C 333/04
[52] U.S. Cl. ................................................... 558/234
[58] Field of Search ....................................... 558/234

[56] References Cited

U.S. PATENT DOCUMENTS

| | | | |
|---|---|---|---|
| 2,884,444 | 4/1959 | Berger et al. | 560/164 |
| 2,901,501 | 8/1959 | Wasson et al. | 558/234 |
| 2,937,119 | 5/1960 | Berger et al. | 514/483 |

*Primary Examiner*—Johann Richter
*Assistant Examiner*—Michael G. Ambrose
*Attorney, Agent, or Firm*—Abelman, Frayne & Schwab

[57] ABSTRACT

There are disclosed 3-thiocarbamoyl-2-phenyl-1,3-propandiol carbamate racemate, represented by the following structural formula I:

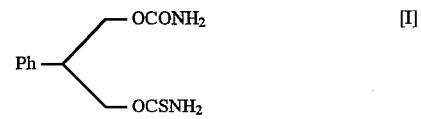

and its (R)- and (S)- optical isomers and intermediates thereof, which are very effective for prophylaxis and treatment of central nervous system disorders including epilepsy and apoplexy. 3-Thiocarbamoyl-2-phenyl-1,3-propandiol carbamate racemate and its (S)- and (R)- optical isomers are prepared from 2-phenyl-1,3-propandiol monothiocarbamate, (S)-2-phenyl-1,3-propandiol monothiocarbamate, and (S)-2-phenyl-1,3-propandiol monocarbamate, respectively.

36 Claims, No Drawings

CARBAMATE COMPOUNDS CONTAINING THIOCARBAMOYL GROUP AND PROCESS FOR PREPARING THE SAME

BACKGROUND OF THE INVENTION

1. Field of the Invention

The present invention relates to novel carbamate compounds derived from 2-phenyl-1,3-propandiol. More particularly, the present invention relates to 3-thiocarbamoyl-2-phenyl-1,3-propandiol carbamates including their racemates and enantiomers, useful to treat the diseases of the central nervous system. Also, the present invention is concerned with a process for preparing the same.

2. Description of the Prior Art

Many reports have disclosed that organic carbamates are effectively used for controlling various central nervous system (CNS) disorders, especially as antiepileptic and centrally acting muscle relaxants.

2-methyl-2-propyl-1,3-propandiol carbamate was first reported in J. Am. Chem. Soc., 73, 5779 (1951), the pharmaceutical activity of which was verified in J. Pharmacol. Exp. Ther., 104, 229 (1952).

In addition, 2-phenyl-1,3-propandiol dicarbamate is disclosed in U.S. Pat. No. 2,884,444 and isopropylmeprobamate in U.S. Pat. No. 2,937,119. These compounds are found to be very effective as therapeutical medicines for managing CNS diseases, such as antiepileptic and centrally acting muscle relaxants, respectively.

Active research and development efforts have been continued to be directed to the application of carbamates for CNS disorders.

SUMMARY OF THE INVENTION

As a result of intensive and thorough research for the derivatives of 2-phenyl-1,3-propandiol, the present inventors found that thiocarbamoyl-containing carbamates are pharmaceutically useful in prophylaxis and treatment of CNS disorders, for example, epilepsy and apoplexy.

In vivo, an optical isomer of one compound may exhibit on even better pharmaceutical effect than other optical isomers, and many examples showing such optical effect have been reported. Thus, it is very important to separate the racemates of one compound into the respective optical isomers and apply them for pharmacology.

Accordingly, it is a principal object of the present invention to provide novel thiocarbamoyl-containing compounds effective for prophylaxis and treatment of CNS disorders, and pharmaceutically acceptable salts thereof.

It is another object of the present invention to provide intermediates useful to synthesize the thiocarbamoyl-containing compounds.

It is another object of the present invention to provide a method for preparing the novel thiocarbamoyl-containing compounds.

It is a further object of the present invention to provide a method for preparing the intermediates useful to synthesize the thiocarbamoyl-containing compounds.

In accordance with an aspect of the present invention, there are provided novel carbamate derivatives pharmacologically excellent for prophylaxis and treatment of CNS disorders: 3-thiocarbamoyl-2-phenyl-1,3-propandiol carbamate racemate, represented by structural formula I;

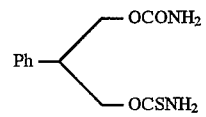

(S)-3-thiocarbamoyl-2-phenyl-1,3-Propandiol carbamate, represented by structural formula II;

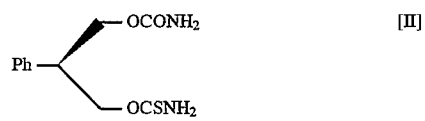

and (R)-3-thiocarbamoyl-2-phenyl-1,3-Propandiol carbamate, represented by structural formula III:

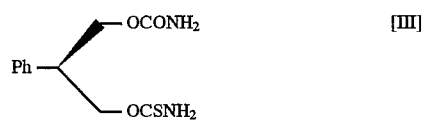

In accordance with another aspect of the present invention, there are provided intermediates useful to synthesize the compounds of structural formulas I, II and III: 2-phenyl-1,3-propandiol monothiocarbamate, represented by structural formula IV;

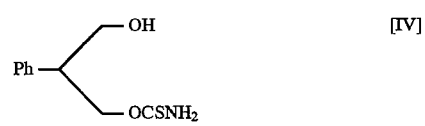

(S)-2-phenyl-1,3-propandiol monothiocarbamate, represented by structural formula V;

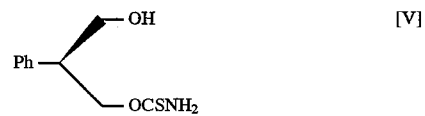

3-acetoxy-2-phenylpropanol thiocarbamate, represented by structural formula VI;

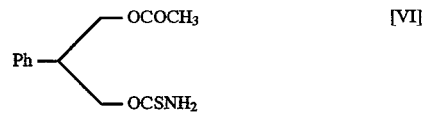

and (S)-3-acetoxy-2-phenylpropanol thiocarbamate, represented by structural formula VII:

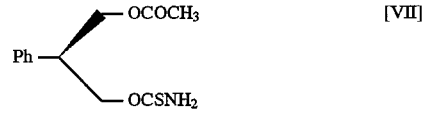

In accordance with another aspect of the present invention, there is provided a method for preparing 3-thiocarbamoyl-2-phenyl-1,3-propandiol carbamate racemate and its (S)- and (R)- optical isomers represented by structural formulas I, II, and III, respectively, within a short time in a high yield and in a high optical purity.

In accordance with a further aspect of the present invention, there is provided a method for preparing intermediates of thiocarbamoyl-containing compounds, 2-phenyl-1,3-propandiol monothiocarbamate, (S)-2-phenyl-1,3propandiol monothiocarbamate, 3-acetoxy-2-phenylpropanol thiocarbamate, and (S)-3-acetoxy-2-phenylpropanol thiocarbamate, represented by structural formulas IV, V, VI, and VII, respectively, within a short time in a high yield and in a high optical purity.

DETAILED DESCRIPTION OF THE INVENTION

Because the novel compound of structural formula I has a chiral center, two optical isomers are possible as mentioned above.

According to the present invention, the compounds of structural formulas I and II are prepared from their respective corresponding intermediates, structural formulas IV and V. This can be done by treating 0.1 to 2 moles of the compounds of structural formulas IV and V with 1.0 to 2.0 molar equivalents of phosgene in the mixed solvent of aromatic hydrocarbon and halogenohydrocarbon in the presence of an amine base, followed by reaction with 1 to 1,000 molar equivalents of ammonia.

Examples of available aromatic hydrocarbon include benzene, toluene, xylene and the like. As for the halogenohydrocarbon used in combination with the aromatic hydrocarbon, chloroform, dichloromethane and trichloroethane is available. Amine base useful in the present invention includes antipyrine, diisopropylethyl amine and pyridine with a preference of antipyrine, a sterically hindered base.

Upon reaction with the compounds of structural formulas IV and V, phosgene, either neat or as solution in toluene, may be used. Likewise, ammonia, either neat or as solution in water or lower alcohol such as methanol or ethanol, may be used.

Both phosgene and ammonia are reacted at temperatures ranging from −10° C. to 10° C.

According to the present invention, the compound of structural formula III is prepared by 0.1 to 2 moles of (S)-2-phenyl-1,3-propandiol monocarbamate, represented by structural formula VIII;

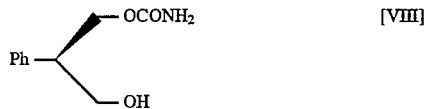

with 1.0 to 2.0 molar equivalents of thiophosgene in a mixed solvent of aromatic hydrocarbon and halogenohydrocarbon in the presence of an amine base and then, with 1 to 1,000 molar equivalents of ammonia, either neat or as solution in water or lower alcohol such as methanol and ethanol.

In this reaction, the aromatic hydrocarbon, halogenohydrocarbon and amine base are the same as those previously mentioned.

As to the intermediates, the compounds of structural formulas IV, V and VIII can be synthesized from the compounds of structural formulas VI and VII, and the following structural formula IX, respectively:

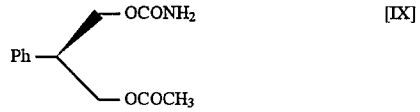

In more detail, the compound represented by structural formula IV can be obtained by hydrolyzing 0.1 to 2.0 moles of the compound of structural formula VI in a mixed solution of 1N sodium hydroxide aqueous solution and ethanol (1:1) at a temperature of 0° to 30° C. The compounds of structural formulas V and VIII can be achieved by hydrolyzing the compounds of structural formulas VII and IX, respectively, in the presence of an enzyme in a phosphate buffer. Preferably, the phosphate buffer is diluted into 0.01 to 0.1M in order to improve the selectivity of reaction, with pH 7. Examples of the enzyme useful for this hydrolysis include lipase extracted from the pancreas of pig (PPL), candida lipase (CCL), aspagilus lipase (ANL), pseudomonas lipase (PSL) and esterase extracted from the liver of pig (PLE), with a preference of PLE. Such hydrolytic reaction is carried out at a temperature of 0° to 30° C.

In accordance with the present invention, the compounds of structural formulas VI and VII can be derived from their respective corresponding intermediates, 3-acetoxy-2-phenylpropanol racemate and (R)-3-acetoxy-2-phenylpropanol. In the presence of amine base, 0.1 to 2.0 moles of each of the intermediates are treated with 1.0 to 2.0 molar equivalents of thiophosgene, followed by the reaction with 1 to 1,000 molar equivalents of ammonia, either neat or as solution in water or a lower alcohol such as methanol or ethanol. Like in the other reactions of the present invention, both thiophosgene and ammonia are reacted at temperatures ranging from −10° C. to 10° C.

As for the compound represented by structural formula IX, a similar procedure is applied, in accordance with the present invention. That is, 0.1 to 2 moles of (R)-3-acetoxy-2-phenylpropanol is treated with 1.0 to 2.0 molar equivalents of phosgene in the presence of amine base in a mixed solvent of aromatic hydrocarbon and halogenohydrocarbon, followed by the reaction with 1 to 1,000 molar equivalents of ammonia. As illustrated above, phosgene and ammonia, either neat or as solution, such as solution in toluene for phosgene and solution in water or a lower alcohol such as methanol and ethanol for ammonia. Also, the aromatic hydrocarbon, halogenohydrocarbon and amine base used in this hydrolysis are the same as those used in the above reactions of the present invention.

A better understanding of the present invention may be obtained in light of following examples which are set forth to illustrate, but are not to be construed to limit, the present invention.

EXAMPLE I

Preparation of 3-Acetoxy-2-phenylpropanol thiocarbamate racemate (Formula VI)

In a 250 mL flask equipped with magnetic stirrer 4.7 g (0.025 mole) of antipyrine, 1.94 g (0.01 mole) of 3-acetoxy-2-phenylpropanol, 80 mL of toluene, and 20 mL of chloroform were placed and stirred at 0° C.

To this solution 1.38 g (0.012 mole) of thiophosgene was added at 0° C. with stirring. The progress of reaction was able to be monitored by generation of precipitates. When five hours passed since the addition of thiophosgene, the reaction was terminated, followed by filtration.

Ammonia gas was injected into the filtrate maintained with a temperature of 0° C. Thereafter, stirring was continued over 30 minutes, followed by the filtration of the solution to remove the precipitates generated.

The filtered solution was distilled in vacuo to evaporate the solvent out and the residue was subjected to column chromatography (ethylacetate:n-hexane=2:3) to give 3-acetoxy-2-phenylpropanol thiocarbamate: Yield 83%.

$^1$H-NMR(CDCL$_3$, 200 MHz), ppm (δ):

2.00(s,3H), 3.38–3.45(m,1H), 4.29–4.33(d,2H), 4.64–4.67 (d,2H), 6.18(b,1H), 6.69(b,1H), 7.25–7.28 (m,5H)

EXAMPLE II

Preparation of (S)-3-Acetoxy-2-phenylpropanol thiocarbamate (Formula VII)

Example I was repeated using (R)-3-acetoxy-2-phenylpropanol as the starting material instead of 3-acetoxy-2-phenylpropanol racemate. The title compound thus obtained was tested for optical purity with a high pressure liquid chromatograph (HPLC) equipped with a column for separating optical isomers.

m.p.=62°–63° C.

$^1$H-NMR(CDCL$_3$, 200 MHz), ppm (δ):

2.00(s,3H), 3.38–3.45(m,1H), 4.29–4.33(d,2H), 4.64–4.67 (d,2H), 6.18(b,1H), 6.69(b,1H), 7.25–7.28(m,5H)

EXAMPLE III

Preparation of 2-Phenyl-1,3-propandiol monothiocarbamate racemate (Formula IV)

In a 100 mL flask equipped with magnetic stirrer 2.53 g (0.01 mole) of 3-acetoxy-2-phenylpropanol thiocarbamate obtained in Example I was placed together with 25 mL of carbonate buffer (pH 10, 0.05M), 25 mL of ethanol and 10 mL of 1N sodium hydroxide aqueous solution with stirring at a room temperature.

The conversion of the reactants was monitored by HPLC. When the conversion was completed, the reaction was terminated, after which ethanol was completely removed by distillation in vacuo. The resulting residue was extracted three times with ethyl acetate.

After being transferred, the organic layer was distilled in vacuo to take off the solvent, and subjected to column chromatography (ethylacetate: n-hexane=1:1), to give 2-phenyl-1,3-propandiol monothiocarbamate: Yield 90%.

m.p.=64°–65° C.

$^1$H-NMR(CDCL$_3$, 200 MHz), ppm (δ):

2.50(b,1H), 3.15–3.39(m,1H), 3.80(d,2H), 4.70(d,2H), 6.35(b,1H), 6.80(b,1H), 7.19–7.35(m,5H)

EXAMPLE IV

Preparation of (S)-2-Phenyl-1,3-propandiol monothiocarbamate (Formula V)

In a 500 mL flask equipped with magnetic stirrer 2.53 g (0.01 mole) of (S)-3-acetoxy-2-phenylpropanol thiocarbamate obtained in Example II was placed together with 200 mL of phosphate buffer (pH 7, 0.014M) and 1.2 g of PLE with stirring at a room temperature.

The conversion of the reactants was monitored by HPLC. When the conversion rate reached about 80% the reaction was terminated, after which filtration was carried out. The filtrate was extracted three times with ethyl acetate.

After being transferred, the organic layer was distilled in vacuo to take off the solvent, and subjected to column chromatography (ethylacetate:n-hexane=1:1), to give (S)-2-phenyl-1,3-propandiol monothiocarbamate, which was then tested for optical purity with HPLC equipped with a column for separating optical isomers: Yield 92%.

$^1$H-NMR(CDCL$_3$, 200 MHz), ppm (δ):

2.50(b,1H), 3.15–3.39(m, 1H) , 3.80(d,2H), 4.70(d,2H), 6.35(b,1H), 6.80(b,1H), 7.19–7.35 (m,5H)

EXAMPLE V

Preparation of 3-Thiocarbamoyl-2-phenyl-1,3-propandiol carbamate racemate (Formula I)

In a 250 mL flask equipped with magnetic stirrer 4.7 g (0.025 mole) of antipyrine, 2.11 g (0.01 mole) of 2-phenyl-1,3-propandiol monothiocarbamate racemate obtained in Example III, 80 mL of toluene and 20 mL of chloroform were placed and stirred at a temperature of 0° C.

To this solution 14 mL of 0.6M phosgene solution was added and stirred at a temperature of 0° C. The progress of reaction could be monitored by generation of precipitates and was terminated 5 hours after the addition. Thereafter, the reaction was filtered.

While being maintained at a temperature of 0° C., the filtrate was treated with ammonia gas over 30 minutes. Stirring was continued over another 30 minutes after which the reaction was filtered to remove the precipitates generated.

The solvent was evaporated out by distilling the resulting solution in vacuo and then was column chromatography (ethylacetate:n-hexane=1:1) carried out, to separate 3-thiocarbamoyl-2-phenyl-1,3-propandiolcarbamate racemate: Yield 83%

$^1$H-NMR(CDCL$_3$, 200 MHz), ppm (δ):

3.35–3.50(m,1H), 4.35(d,2H) , 4.67(d,2H), 4.67(d,2H) 4.78(b,2H), 6.21(b,1H), 6.62(b,1H), 7.21–7.37(m,5H)

EXAMPLE VI

Preparation of (S)-3-Thiocarbamoyl-2-phenyl-1,3-propandiol carbamate (Formula II)

Example V was repeated using as the starting material (S)-2-phenyl-1,3-propandiol monothiocarbamate prepared in Example IV, instead of 2-phenyl-1,3-propandiol monothiocarbamate racemate. The title compound thus obtained was tested for optical purity with a high pressure liquid chromatograph equipped with a column for separating optical isomers.

m.p.=108.5°–109.0° C.

$^1$H-NMR(CDCL$_3$, 200 MHz), ppm (δ):

3.35–3.50(m,1H), 4.35(d,2H) , 4.67 (d,2H), 4.67(d,2H) , 4.78(b,2H) , 6.21(b,1H), 6.62(b,1H) , 7.21–7.37 (m,5H)

EXAMPLE VII

Preparation of (R)-3-Thiocarbamoyl-2-phenyl-1,3-propandiol carbamate (Formula III)

In a 250 mL flask equipped with magnetic stirrer 4.7 g (0.025 mole) of antipyrine, 1.95 g (0.01 mole) of (S)-2-phenyl-1,3-propandiol monocarbamate, 80 mL of toluene and 20 mL of chloroform were placed and stirred at a temperature of 0° C.

To this solution 1.38 g (0.012 mole) of thiophosgene was added and stirring continued at a temperature of 0° C. The progress of reaction could be monitored by generation of precipitates and was terminated 5 hours after the addition. Thereafter, the reaction was filtered.

While being maintained at a temperature of 0° C., the filtrate was treated with ammonia gas over 30 minutes. Stirring was continued over another 30 minutes after which the reaction was filtered to remove the precipitates generated.

The solvent was evaporated out by distilling the resulting solution in vacuo and then was column chromatography (ethylacetate:n-hexane=1:1) carried out, to separate (R)-3-thiocarbamoyl-2-phenyl-1,3-propandiolcarbamate: Yield 83 %.

The title compound thus obtained was tested for optical purity with a high pressure liquid chromatograph equipped with a column for separating optical isomers.

m.p.=113.5°–114.0° C.

$^1$H-NMR(CDCL$_3$, 200 MHz), ppm ($\delta$):

3.35–3.50(m,1H), 4.35(d,2H), 4.67 (d,2H), 4.67 (d,2H) 4.78(d,2H), 6.21(b,1H), 6.62(b,1H), 7.21–7.37(m,5H)

Other features, advantages and embodiments of the present invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. 3-Thiocarbamoyl-2-phenyl-1,3-propandiol carbamate, represented by the following structural formula I:

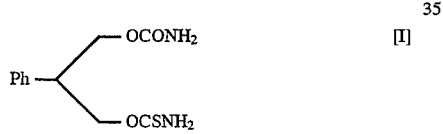

2. (S)-3-Thiocarbamoyl-2-phenyl-1,3-propandiol carbamate, represented by the following structural formula II:

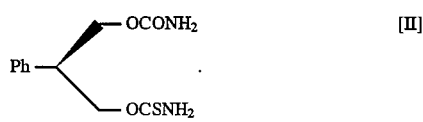

3. (R)-3-Thiocarbamoyl-2-phenyl-1,3-propandiol carbamate, represented by the following structural formula III:

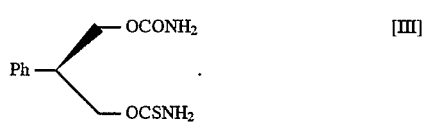

4. 2-Phenyl-1,3-propandiol monothiocarbamate, represented by the following structural formula IV:

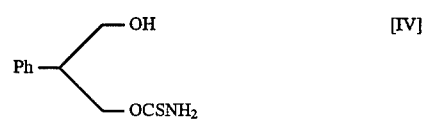

5. (S)-2-Phenyl-1,3-propandiol monothiocarbamate, represented by the following structural formula V:

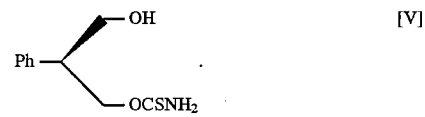

6. 3-Acetoxy-2-phenylpropanol thiocarbamate, represented by the following structural formula VI:

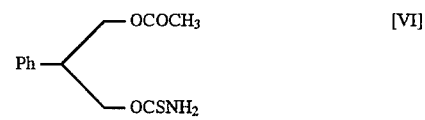

7. (S)-3-Acetoxy-2-phenylpropanol thiocarbamate, represented by the following structural formula VII:

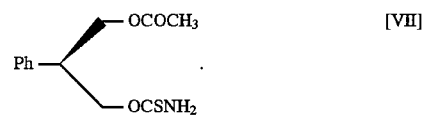

8. A method for preparing 3-thiocarbamoyl-2-phenyl-1,3-propandiol carbamate, represented by the following structural formula I:

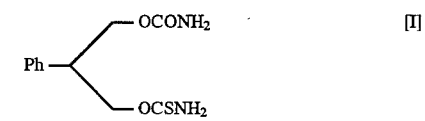

which comprises treating 2-phenyl-1,3-propandiol monothiocarbamate, represented by the following structural formula IV:

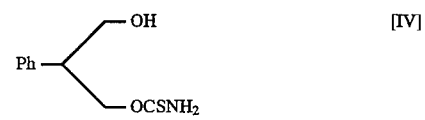

with phosgene in a mixed solvent of aromatic hydrocarbon and halogenohydrocarbon in the presence of amine base and subsequently with ammonia to prepare 3-thiocarbamoyl-2-phenyl-1,3-propandiol carbamate within a short time in a high yield.

9. The method in accordance with claim 8, wherein said aromatic hydrocarbon is selected from the group consisting of benzene, toluene and xylene.

10. The method in accordance with claim 8, wherein said halogenohydrocarbon is selected from the group consisting of chloroform, dichloromethane and trichloroethane.

11. The method in accordance with claim 8, wherein said amine base is selected from the group consisting of antipyrine, diisopropylethylamine and pyridine.

12. The method in accordance with claim 8, wherein the treatment with phosgene is carried out at a temperature of −10° C. to 10° C.

13. The method in accordance with claim 8, wherein the treatment with ammonia is carried out at a temperature of −10° C. to 10° C.

14. A method for preparing (S)-3-thiocarbamoyl-2-phenyl-1,3-propandiol carbamate, represented by the following structural formula II:

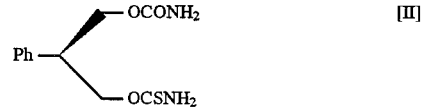

which comprises treating (S)-2-phenyl-1,3-propandiol monothiocarbamate, represented by the following structural formula V:

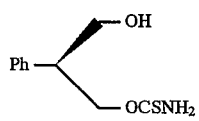

with phosgene in a mixed solvent of aromatic hydrocarbon and halogenohydrocarbon in the presence of amine base and subsequently with ammonia to prepare (S)-3-thiocarbamoyl-2-phenyl-1,3-propandiol carbamate within a short time in a high yield and in a high purity.

15. The method in accordance with claim 14, wherein said aromatic hydrocarbon is selected from the group consisting of benzene, toluene and xylene.

16. The method in accordance with claim 14, wherein said halogenohydrocarbon is selected from the group consisting of chloroform, dichloromethane and trichloroethane.

17. The method in accordance with claim 14, wherein said amine base is selected from the group consisting of antipyrine, diisopropylethylamine and pyridine.

18. The method in accordance with claim 14, wherein the treatment with phosgene is carried out at a temperature of −10° C. to 10° C.

19. The method in accordance with claim 14, wherein the treatment with ammonia is carried out at a temperature of −10° C. to 10° C.

20. A method for preparing (R)-3-thiocarbamoyl-2-phenyl-1,3-propandiol carbamate, represented by the following structural formula III:

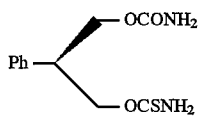

which comprises treating (S)-2-phenyl-1,3-propandiol monocarbamate, represented by the following structural formula VIII:

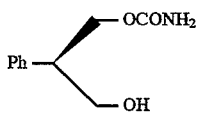

with thiophosgene in a mixed solvent of aromatic hydrocarbon and halogenohydrocarbon in the presence of amine base and subsequently with ammonia to prepare (R)-3-thiocarbamoyl-2-phenyl-1,3-propandiol carbamate within a short time in a high yield and in a high purity.

21. The method in accordance with claim 20, wherein said aromatic hydrocarbon is selected from the group consisting of benzene, toluene and xylene.

22. The method in accordance with claim 20, wherein said halogenohydrocarbon is selected from the group consisting of chloroform, dichloromethane and trichloroethane.

23. The method in accordance with claim 20, wherein said amine base is selected from the group consisting of antipyrine, diisopropylethylamine and pyridine.

24. The method in accordance with claim 20, wherein the treatment with thiophosgene is carried out at a temperature of −10° C. to 10° C.

25. The method in accordance with claim 20, wherein the treatment with ammonia is carried out at a temperature of −10° C. to 10° C.

26. A method for preparing 2-phenyl-1,3-propandiol monothiocarbamate, represented by the following structural formula IV:

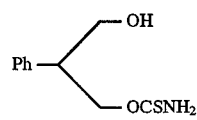

which comprises hydrolysing 3-acetoxy-2-phenylpropanol thiocarbamate, represented by the following structural formula VI:

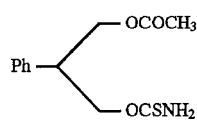

in a mixture of sodium hydroxide aqueous solution and ethanol to prepare 2-phenyl-1,3-propandiol monothiocarbamate within a short time in a high yield.

27. A method for preparing (S)-2-phenyl-1,3-propandiol monothiocarbamate, represented by the following structural formula V:

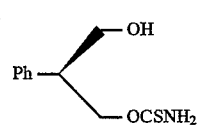

which comprises hydrolysing (S)-3-acetoxy-2-phenylpropanol thiocarbamate in a phosphate buffer in the presence of an enzyme to prepare (S)-2-phenyl-1,3-propandiol monothiocarbamate within a short time in a high yield and in a high optical purity.

28. The method in accordance with claim 27, wherein said enzyme is selected from the group consisting of lipase extracted from the pancreas of pig, candida lipase, aspagilus lipase, pseudomonas lipase and esterase extracted from the liver of pig.

29. The method in accordance with claim 27, wherein the hydrolysis is carried out at a temperature of 0° to 30° C.

30. The method in accordance with claim 27, wherein said buffer has a pH value of 7.

31. A method for preparing 3-acetoxy-2-phenylpropanol thiocarbamate, represented by the following structural formula VI:

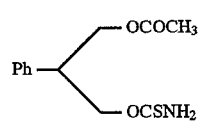

which comprises treating 3-acetoxy-2-phenylpropanol with thiophosgene in a mixed solvent of aromatic hydrocarbon and halogenohydrocarbon in the presence of amine base and subsequently with ammonia to prepare 3-acetoxy-2-phenylpropanol thiocarbamate within a short time in a high yield.

32. The method in accordance with claim 31, wherein the treatment with thiophosgene is carried out at a temperature of −10° C. to 10° C.

33. The method in accordance with claim 31, wherein the treatment with ammonia is carried out at a temperature of −10° C. to 10° C.

34. A method for preparing (S)-3-acetoxy-2-phenylpropanol thiocarbamate, represented by the following structural formula VII:

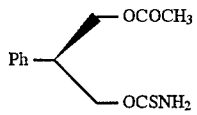 [VII]

which comprises treating (R)-3-acetoxy-2-phenylpropanol with thiophosgene in a mixed solvent of aromatic hydrocarbon and halogenohydrocarbon in the presence of amine base and subsequently with ammonia to prepare (S)-3-acetoxy-2-phenylpropanol thiocarbamate within a short time in a high yield and in a high optical purity.

35. The method in accordance with claim 34, wherein the treatment with thiophosgene is carried out at a temperature of −10° C. to 10° C.

36. The method in accordance with claim 34, wherein the treatment with ammonia is carried out at a temperature of −10° C. to 10° C.

* * * * *